US010052045B2

(12) United States Patent
Hao et al.

(10) Patent No.: US 10,052,045 B2
(45) Date of Patent: Aug. 21, 2018

(54) METHOD FOR TESTING ORAL MALODOR

(71) Applicant: Colgate-Palmolive Company, Piscataway, NJ (US)

(72) Inventors: Zhigang Hao, Bridgewater, NJ (US); Deborah A. Peru, Lebanon, NJ (US); Joe Vazquez, Hamilton, NJ (US); Jessica Monk, Hoboken, NJ (US); Harsh M. Trivedi, Hillsboro, NJ (US); Paul Joseph Vincenti, Jefferson, NJ (US); Osman Khalid, Hamilton, NJ (US)

(73) Assignee: Colgate-Palmolive Company, New York, NY (US)

( * ) Notice: Subject to any disclaimer, the term of this patent is extended or adjusted under 35 U.S.C. 154(b) by 40 days.

(21) Appl. No.: 14/441,184

(22) PCT Filed: Dec. 21, 2012

(86) PCT No.: PCT/US2012/071262
§ 371 (c)(1),
(2) Date: May 7, 2015

(87) PCT Pub. No.: WO2014/098895
PCT Pub. Date: Jun. 26, 2014

(65) Prior Publication Data
US 2015/0265183 A1  Sep. 24, 2015

(51) Int. Cl.
| A61K 8/33 | (2006.01) |
| A61B 5/08 | (2006.01) |
| A61K 8/35 | (2006.01) |
| A61Q 11/00 | (2006.01) |
| G01N 33/497 | (2006.01) |
| A61B 10/00 | (2006.01) |
| A61K 8/55 | (2006.01) |

(52) U.S. Cl.
CPC ............... *A61B 5/08* (2013.01); *A61B 5/082* (2013.01); *A61B 10/00* (2013.01); *A61K 8/33* (2013.01); *A61K 8/35* (2013.01); *A61K 8/55* (2013.01); *A61Q 11/00* (2013.01); *G01N 33/497* (2013.01); *A61B 2010/0087* (2013.01); *G01N 2033/4975* (2013.01); *Y10T 436/182* (2015.01)

(58) Field of Classification Search
CPC ..................................................... A61K 8/33
See application file for complete search history.

(56) References Cited

U.S. PATENT DOCUMENTS

| 2003/0008407 A1 | 1/2003 | Fu |
| 2003/0100842 A1 | 5/2003 | Rosenberg et al. |
| 2004/0076854 A1 | 4/2004 | Satou et al. |
| 2008/0091085 A1 | 4/2008 | Urushihata et al. |
| 2011/0239736 A1 | 10/2011 | Ramji et al. |

FOREIGN PATENT DOCUMENTS

| DE | 10137564 | 2/2003 |
| JP | 60004859 | 1/1985 |
| WO | WO 97/05482 | 2/1997 |
| WO | WO 02/066976 | 8/2001 |
| WO | WO 2007/026644 | 2/2007 |
| WO | WO 2008/114338 | 9/2008 |
| WO | WO 2011/123601 | 10/2011 |
| WO | WO 2012/033455 | 3/2012 |

OTHER PUBLICATIONS

Van den Velde et al (J Dent Res 88(3) 2009).*
Ongole et al (Kathmandu University Medical Journal (2010), vol. 8, No. 2, Issue 30, 269-275).*
Smith and March, March's Advanced Organic Chemistry—Reactions, Mechanisms and Structure (6th Edition), p. 1277 (2007).
Per Stanley Thrane et al., "A new mouthrinse combining zinc and chlorhexidine in low concentrations provides superior efficacy against halitosis compared to existing formulations: a double-blind clinical study," The Journal of Clinical Dentistry, Jan. 2007, 18(3):82-86.
International Search Report and Written Opinion for International Application No. PCT/US2012/071262 dated Dec. 4, 2013.

* cited by examiner

*Primary Examiner* — Benjamin Packard

(57) ABSTRACT

The present invention relates to a method for testing oral malodor, in particular oral malodor from onion and garlic. Described herein are methods for testing the efficacy of an oral care composition to reduce oral malodor, the method comprising the steps of: a) cleaning at least a part of the oral cavity with an oral care composition; b) testing a first sample of exhaled breath from the cleaned oral cavity to provide a first test result representing a first amount of at least one oral malodor component detected in the exhaled breath; c) exposing the oral cavity to an oral malodor material including or capable of forming the at least one oral malodor component; and d) testing a second sample of exhaled breath from the oral cavity to provide a second test result representing a second amount of the at least one oral malodor component detected in the exhaled breath.

6 Claims, No Drawings

METHOD FOR TESTING ORAL MALODOR

BACKGROUND OF THE INVENTION

Incorporation of onions or garlic into the diet is believed to provide beneficial therapeutic effects due to the presence of various antioxidants, bioflavanoids and sulfide compounds. However, the presence of sulfide compounds usually is associated with bad breath or halitosis which makes onion or garlic malodor undesirable. It is known that some individuals have particular diets which can result in those individuals having a tendency to suffer from excessive onion or garlic malodor in their breath.

It is known to provide oral care compositions, such as dentifrice, toothpaste, mouthrinse or mouthwash, which have been specially formulated to counteract onion or garlic malodor. A large number of potential active components or blends are known to be incorporated into oral care compositions for this purpose. Nevertheless, there is still a need for more effective oral care compositions and active components for effectively combatting oral malodor from onion or garlic. There is correspondingly a need for further research and development to develop such oral care compositions.

When an oral care composition is being formulated specifically to target oral malodor from onion or garlic, there is a very wide choice of potential active components and component combinations, as well as component amounts. Furthermore, there is often confusion from the user as to whether the malodor reduction is being achieved by odor masking (overwhelming the malodor with another odor) or by elimination or conversion of the malodorous compound into a less malodorous compound, the latter being the preferred means of addressing malodor.

Furthermore, the choice of potential vehicles and other active components for providing efficacy for other technical effects, such as anti-cavity protection, anti-plaque efficacy, and anti-microbial efficacy, is extremely wide.

It is not possible to predict with any degree of certainty how effective any particularly formulated oral care composition may be against oral malodor from onion or garlic. Consequently, each formulation must be individually tested for efficacy against oral malodor from onion or garlic.

Such testing is time consuming, laborious and costly. Furthermore, it is difficult to achieve consistent and robust quantitative results which can be used as a reliable tool during the research and development process.

There is a need for a testing method which can efficiently and reliably test oral care compositions to determine how effective any particularly formulation may be against oral malodor, for example from onion or garlic.

There is also a need for such a testing method which is less time consuming, less laborious and less costly than known testing methods.

Furthermore, there is a need for a testing method which can readily achieve consistent and robust quantitative results which can be used as a reliable tool during the research and development process for the oral care composition having the desired efficacy.

SUMMARY OF THE INVENTION

The invention addresses the above needs in the art by providing a method for testing the efficacy of an oral care composition to reduce oral malodor, the method comprising at least the steps of:

cleaning at least a part of the oral cavity with an oral care composition and testing the cleaned oral cavity to provide a baseline amount of at least one oral malodor component detected in the exhaled breath;

exposing the oral cavity to an oral malodor material containing at least one oral malodor component;

obtaining a sample of exhaled breath from the oral cavity to detect a first amount of the at least one oral malodor component in the exhaled breath which is a representation of the prophylactic effect of the oral care composition;

optionally, comparing the amount of the at least one oral malodor component detected in the exhaled breath after cleansing with an oral care composition with an amount from cleansing with a different oral care composition and selecting the oral care composition with the lower amount for a method of providing prophylactic effect against at least one malodor component in the oral cavity;

cleaning at least a part of the oral cavity with the oral care composition;

obtaining a sample of exhaled breath from the oral cavity to detect an amount of the at least one oral malodor component in the exhaled breath which is a representation of the efficacy of the oral care composition to reduce oral malodor; and optionally, comparing the amount of the at least one oral malodor component detected in the exhaled breath after cleansing with an oral care composition with an amount from cleansing with a different oral care composition and selecting the oral care composition with the lower amount for a method of reducing at least one malodor component in the oral cavity.

As used throughout, ranges are used as shorthand for describing each and every value that is within the range. Any value within the range can be selected as the terminus of the range.

Further embodiments of the invention will be apparent from the detailed description and the examples.

DESCRIPTION OF THE INVENTION

Accordingly, the invention provides a method for testing the efficacy of an oral care composition to reduce oral malodor, the method comprising the steps of:

a1. cleaning at least a part of the oral cavity with an oral care composition and testing the cleaned oral cavity to provide a baseline amount of at least one oral malodor component detected in the exhaled breath;

b1. exposing the oral cavity to an oral malodor material containing the at least one oral malodor component;

c1. obtaining a sample of exhaled breath from the oral cavity to detect an amount of the at least one oral malodor component in the exhaled breath which is a representation of the prophylactic effect of the oral care composition; and d1. comparing the amount of the at least one oral malodor component detected in the exhaled breath after cleansing with an oral care composition with an amount from cleansing with a different oral care composition and selecting the oral care composition with the lower amount for a method of providing prophylactic effect against at least one malodor component in the oral cavity.

Another aspect of the invention provides a method for testing the efficacy of and selecting an oral care composition to reduce oral malodor, wherein the method comprises the steps of:

e1. exposing the oral cavity to an oral malodor material containing the at least one oral malodor component;

f1. cleaning at least a part of the oral cavity with the oral care composition;

g1. obtaining a sample of exhaled breath from the oral cavity to detect an amount of the at least one oral malodor component in the exhaled breath which is a representation of the efficacy of the oral care composition to reduce oral malodor; and h1. comparing the amount of the at least one oral malodor component detected in the exhaled breath after cleansing with an oral care composition in step e1 with a amount from cleansing with a different oral care composition and selecting the oral care composition with the lower amount for a method of reducing at least one malodor component in the oral cavity.

Another aspect of the invention provides a method for testing the efficacy of and selecting an oral care composition to reduce oral malodor, wherein the method comprises the steps of:

a2. cleaning at least a part of the oral cavity with an oral care composition and testing the cleaned oral cavity to provide a baseline amount of at least one oral malodor component detected in the exhaled breath;

b2. exposing the oral cavity to an oral malodor material containing the at least one oral malodor component;

c2. obtaining a sample of exhaled breath from the oral cavity to detect a amount of the at least one oral malodor component in the exhaled breath which is a representation of the prophylactic effect of the oral care composition;

d2. optionally, comparing the amount of the at least one oral malodor component detected in the exhaled breath after cleansing with an oral care composition with a amount from cleansing with a different oral care composition and selecting the oral care composition with the lower amount for a method of providing prophylactic effect against at least one malodor component in the oral cavity;

e2. cleaning at least a part of the oral cavity with the oral care composition from step a2;

f2. obtaining a sample of exhaled breath from the oral cavity to detect an amount of the at least one oral malodor component in the exhaled breath which is a representation of the efficacy of the oral care composition to reduce oral malodor; and g2. optionally, comparing the amount of the at least one oral malodor component detected in the exhaled breath after cleansing with an oral care composition in step e2 with a amount from cleansing with a different oral care composition and selecting the oral care composition with the lower amount for a method of reducing at least one malodor component in the oral cavity.

Another aspect of the invention provides a method for testing the efficacy of and selecting an oral care composition to reduce oral malodor, wherein the method comprises the steps of:

a2. cleaning at least a part of the oral cavity with an oral care composition and testing the cleaned oral cavity to provide a baseline amount of at least one oral malodor component detected in the exhaled breath;

b2. exposing the oral cavity to an oral malodor material containing the at least one oral malodor component;

c2. obtaining a sample of exhaled breath from the oral cavity to detect an amount of the at least one oral malodor component in the exhaled breath which is a representation of the propylactic effect of the oral care composition;

d2. comparing the amount of the at least one oral malodor component detected in the exhaled breath after cleansing with an oral care composition with a amount from cleansing with a different oral care composition and selecting the oral care composition with the lower amount for a method of providing prophylactic effect against at least one malodor component in the oral cavity;

e2. cleaning at least a part of the oral cavity with the oral care composition from step a2;

f2. obtaining a sample of exhaled breath from the oral cavity to detect a amount of the at least one oral malodor component in the exhaled breath which is a representation of the efficacy of the oral care composition to reduce oral malodor; and g2. comparing the amount of the at least one oral malodor component detected in the exhaled breath after cleansing with an oral care composition in step e2 with a amount from cleansing with a different oral care composition and selecting the oral care composition with the lower amount for a method of reducing at least one malodor component in the oral cavity.

Optionally, the oral malodor material is selected from at least one of onion and garlic.

Optionally, the oral care composition according to the invention is a dentifrice, mouthwash, mouthrinse, toothpaste, gel, dental cream, chewing gum, or portable dosage article such as, without limitation, a lozenge, a mint, bead, wafer, lollipop, liquid formulated for oral application in a small portable nebulizer (spray bottle), liquid formulated for oral application in a small portable drop-generating bottle, or a soft pliable tablet ("chewie").

In some embodiments, each cleaning step comprises brushing the teeth with the oral care composition which is a toothpaste or dentifrice gel.

In some alternative embodiments, each cleaning step comprises rinsing the oral cavity with the oral care composition which is a mouthwash or mouthrinse.

Optionally, the malodor component is a sulfide compound with the exception of sulfide compounds with a heterocyclic ring as a moiety.

Optionally, the malodor component tested is at least one oral malodor component selected from the group consisting of ethanethiol, dimethyl sulfide, 3,4-dimethylthiophene, methyl-1-propenyl disulfide, trimethyl sulfide, dipropyl sulfide and 3-mercapto-2-mercaptomethyl propanoic acid. (Chemical structures depicted in Table 1 below)

TABLE 1

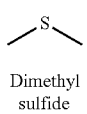
Dimethyl sulfide

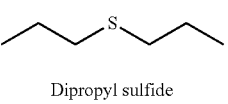
Dipropyl sulfide

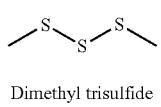
Dimethyl trisulfide

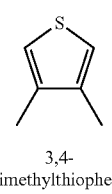
3,4-dimethylthiophene

TABLE 1-continued

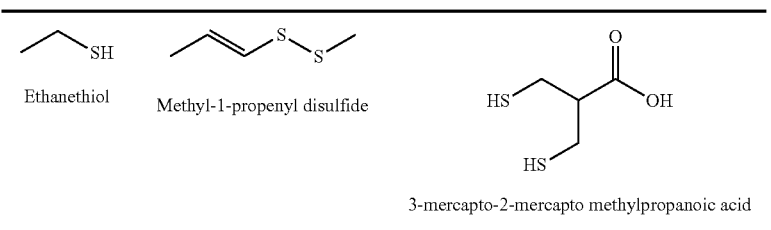

Ethanethiol  Methyl-1-propenyl disulfide  3-mercapto-2-mercapto methylpropanoic acid Further optionally, each testing step tests to detect at least three of the oral malodor components selected from ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

Still further optionally, each testing step tests to detect all of the oral malodor components selected from ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

In an embodiment of the invention, the oral care compositions may comprise carbonyl compounds such as aldehydes and ketones in order to convert the sulfide compounds into less odorous compounds (see general scheme below):

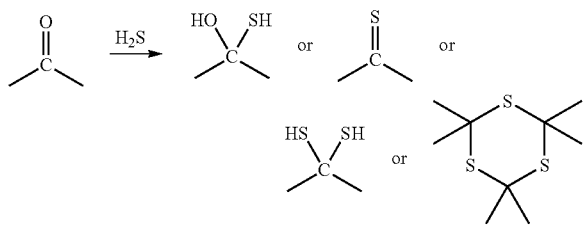

See also *March's Advanced Organic Chemistry—Reactions, Mechanisms and Structure* (6$^{th}$ Edition), ed. Michael B. Smith and Jerry March, pg. 1277 (2007).

In another embodiment of the invention, the oral care compositions may comprise one or more of carbonyl compounds such as aldehydes and ketones, compounds which encapsulate the sulfide compounds, tetrasodium pyrophospate, flavorants and combinations thereof.

Optionally, each obtaining step includes the sub-steps of:
i. collecting the at least one oral malodor component on solid phase micro extraction (SPME) fibers;
ii. separating the collected at least one oral malodor component using chromatography; and
iii. determining an amount of the separated at least one oral malodor component using mass spectrometry to provide a quantification representing an amount of the at least one oral malodor component in the respective sample of exhaled breath.

Optionally, the chromatography is gas phase chromatography (GC) and/or the mass spectrometry (MS) is triple quadrupole mass spectrometry.

Optionally, step b1 or b2 is carried out from 10 to 30 minutes after step a1 or a2, respectively, step c1 or c2 is carried out from 15 to 45 minutes after step a1 or a2, respectively, and step e1 or e2 is carried out from 30 to 60 minutes after step a1 or a2, respectively.

In one embodiment of the invention, the oral care composition selected in step d1 or d2 is different than the original oral care composition selected in step a1 or a2.

In one embodiment of the invention, the oral care composition selected in step g1 or g2 is different than the original oral care composition selected in step a1 or a2.

Consequently, the preferred embodiments of the invention provide a testing protocol, using associated instruments, to effectively measure onion malodor ingredients in the human mouth and to screen the efficacy of oral care compositions with onion malodor reducing function.

The preferred embodiments of the invention also provide an analytical method to measure onion malodor in the mouth, in particular the headspace of the oral cavity, with an in vivo solid phase micro extraction (SPME) technique using chromatography, in particular gas phase chromatography, and mass spectrometry, in particular triple quadrupole mass spectrometry.

The preferred embodiments of the method of the invention can effectively indicate the concentration level of up to seven onion odor ingredients in the human mouth and be used to screen the efficacy of oral care products with an onion malodor reduction function.

The preferred embodiments of the method of the invention can provide an in vivo method capable of differentiation between a control oral care composition, such as a toothpaste and a test oral care composition, such as a toothpaste, specially formulated for the prevention and removal of onion odor from the oral cavity.

In some embodiments, the present invention provides a method for testing the efficacy of an oral care composition to reduce oral malodor. In the testing method, the oral malodor is generated by malodor material, for example being selected from at least one of onion and garlic. Typically, the oral malodor material comprises a measured dose of the oral malodor material, which is typically in a convenient and reproducible form, such as a powder or extract, although raw or natural material may be employed.

The invention has particular application in the testing for efficacy to reduce onion and/or garlic malodor. However, the invention may also be used to test for other oral malodor materials or components.

In one aspect, the method can provide an indication of the ability of an oral care composition prophylactically to reduce oral malodor resulting from the oral malodor material.

A freshness test is initially carried out on the cleaned oral cavity, in which a sample of exhaled breath is tested for the predetermined oral malodor component(s) present in the headspace of the cleaned mouth. Then the oral cavity is exposed to a dose of the oral malodor material, and a further sample of exhaled breath is tested for the predetermined oral malodor component(s) present in the headspace of the odoriferous mouth.

A comparison of the two samples of exhaled breath indicates the ability of the oral care composition prophylactically to prevent the mouth headspace from subsequently having malodors resulting from earlier onion/garlic exposure.

First Cleaning of the Mouth Headspace

In a first step, the method cleans at least a part of the oral cavity with an oral care composition to be tested. The cleaning step typically comprises brushing the teeth with the oral care composition, which is a toothpaste or dentifrice gel. Alternatively, the cleaning step may comprise rinsing the oral cavity with the oral care composition, which is a mouthwash or mouthrinse. The cleaning step preferably has a predetermined time period, and for example may take from 30 seconds to 2 minutes, typically about 1 minute.

Sampling of the Cleaned Mouth Headspace

The procedures described in this sampling and detection technique for verifying the cleansing of the mouth is also used generally in the invention for other sampling and detections steps.

A sample of exhaled breath from the cleaned oral cavity is tested to determine a baseline level of at least one oral malodor component detected in the exhaled breath which should be zero or at low levels of malodor components.

In this embodiment, the testing step collects the at least one oral malodor component on solid phase micro extraction (SPME) fibers. The volunteer human subject in the testing protocol puts a SPME fiber assembly 2 to their mouth M. The fiber assembly 2 is prevented from direct contact with the mouth by a spacer tube 4 of polymeric material. The fiber assembly 2 may typically comprise fused silica fibers having a 75 micron coating of Carboxen®/polydimethylsiloxane (CAR/PDMS) as the matrix active group, a suitable fibre assembly 2, having a black plain hub, being available from Supelco, of Bellefonte, Pa., USA. However, other commercially available SPME fibre assemblies may be employed. The volunteer human subject breathes in through the nose and out through the mouth into the tube 4 and fiber assembly 2.

Then, the oral malodor component(s) collected in the fiber assembly 2 are separated using chromatography, typically gas phase chromatography.

For example, in one embodiment, a gas chromatograph (GC) sold under the trade name GC7890A by Agilent Technologies, Palo Alto, Calif., USA is used. However, other commercially available gas chromatograph equipment may be employed.

In one example, in the gas chromatograph the oven temperature is held at 35° C. for 1 minute, and then the temperature is increased to 160° C. at a 15° C./min rate and held there for another 2.667 minutes. The total running time may be 12 minutes. Helium may be used as the carrier gas and the flow rate may be 1 mL/min. The injector temperature may be set up at 250° C. A SLBTM-5 ms GC column (30 m×0.25 mm×0.25 µm film thickness, available from Sigma-Aldrich, Bellefonte, Pa.) may be used for the separation of the oral malodor component(s) collected in the fiber assembly 2.

After the oral malodor component(s) collected in the fiber assembly 2 have been separated, an amount of the separated oral malodor component(s) is determined using mass spectrometry to provide a quantification representing an amount of the at least one oral malodor component in the sample of exhaled breath.

Typically, the mass spectrometer comprises a 7000MS Triple Quadrupole Mass Spectrometer available from Agilent Technologies, Palo Alto, Calif., USA. However, other commercially available mass spectrometer equipment may be employed.

Typical parameter settings on the mass spectrometer are as follows. The non-ionization for solvent delay may be from 0 to 0.5 minutes. The mass spectrometry detection may be switched on at 0.5 minutes.

The mass spectrometer records a plurality of counts at a respective acquisition time for each component detected. The method of the invention may be used to detect only a single component. However, in the preferred embodiments, plural components are detected, each having a respective acquisition time, and the counts at each acquisition time represents the amount of the respective component present.

In some embodiments, in which the method is for detecting onion and/or garlic malodor, the at least one oral malodor component to be detected is selected from at least one of ethanethiol, dimethyl sulfide, 3, 4-dimethylthiophene, methyl-1-propenyl disulfide, trimethyl sulfide, dipropyl sulfide and 3-mercapto-2-mercaptomethyl propanoic acid. In one embodiment, at least two of those seven oral malodor components, and in another embodiment seven oral malodor components are individually detected.

When these particular oral malodor components are detected using the 7000MS Triple Quadrupole Mass Spectrometer and the typical parameter settings as set out above, the acquisition times are as follows:

From 0.5 to 3.0 minutes, ethanethiol may be detected with a precursor ion at 57.8 and product ion at 31.3 and the collision energy was 20 eV. From 3.0 to 4.5 minutes, dimethyl sulfide may be detected with a precursor ion at 93.7 m/z and product ion at 79.0 m/z and the collision energy was 20 eV. From 4.5 to 5.4 minutes, 3, 4-dimethylthiophene may be detected with a precursor ion at 110.8 m/z and product ion at 77.1 m/z and the collision energy was 20 eV. From 5.4 to 5 8 minutes, methyl-1-propenyl disulfide may be detected with a precursor ion at 119.7 m/z and product ion at 75.1 m/z and the collision energy was 10 eV. From 5.8 to 6.3 minutes, dimethyl trisulfide may be detected with a precursor ion at 125.7 m/z and product ion at 79.0 m/z and the collision energy was 20 eV. From 6.3 to 7.7 minutes, dipropyl sulfide may be detected with a precursor ion at 149.7 m/z and product ion at 43.2 m/z and the collision energy was 10 eV. From 7.7 to 8 5 minutes, 3-mercapto-2-mercapto methyl propanoic acid may be detected with a precursor ion at 151.7 m/z and product ion at 88.0 m/z and the collision energy was 10 eV. The count total of each component is recorded to indicate the amount of that component which has been detected. The counts of two or all of the components may be added to provide a unitary parameter representing the oral malodor from the combination of the respective components.

In some embodiments, the testing step further includes the sub-step of adding together the counts representing the amounts of at least two or all of the detected oral malodor components in the respective sample of exhaled breath to provide a single quantified total count value for the sample of exhaled breath. The single quantified total count value represents oral malodor associated with the oral malodor material in the cleaned mouth headspace.

Introducing Oral Malodor Material into the Mouth

Thereafter, the oral cavity is exposed to an oral malodor material including or capable of forming the at least one oral malodor component. Typically, the oral malodor material comprises a measured dose. Typically, the exposure to oral malodor material is carried out from 10 to 30 minutes, more typically about 20 minutes, after the commencement of the initial cleaning of the oral cavity.

For example, to prepare a measured dose of onion malodor material, approximately 0.5 gram of onion powder may be suspended in 5 mL water, sonicated for 2 minutes, and filtered with a 0.45 μm PTFE filter.

The onion odor may be introduced into the oral cavity by rinsing the mouth with 3 mL of that onion malodor solution for 1 minute.

First Sampling of the Oral Malodor Material-Containing Mouth Headspace

A sample of exhaled breath from the oral malodor material-treated oral cavity is tested to provide a test result representing an amount of at least one oral malodor component detected in the exhaled breath. Optionally, the sample is taken at a period from 15 to 45 minutes after the commencement of the initial cleaning step.

The testing was carried out as described above for the sampling of the cleaned mouth headspace, i.e. a SPME fiber assembly 2 is used, and then the same gas chromatograph and mass spectrometry procedures are carried out as described above. This sampling of the oral malodor material containing mouth headspace provides a plurality of counts at a respective acquisition time for each component detected.

Again, the method of the invention may be used to detect only a single component. However, in other embodiments, plural components are detected, each having a respective acquisition time, and the counts at each acquisition time represents the amount of the respective component present. In some embodiments, the testing step adds together the counts representing the amounts of at least two or all of the detected oral malodor components in the respective sample of exhaled breath to provide a single quantified total count value for the sample of exhaled breath. The single quantified total count value represents oral malodor associated with the oral malodor material in the oral malodor material-containing mouth headspace.

The test result may be compare with the baseline result to provide an indication of the ability of the oral care composition prophylactically to reduce oral malodor resulting from the oral malodor material.

Second Cleaning of the Mouth Headspace

In a further aspect, the method further provides an indication of the ability of the oral care composition to refresh the oral cavity and reduce oral malodor resulting from previous exposure to the oral malodor material.

Thereafter, in order to determine the refresh-ability of the oral care composition, the method again cleans at least a part of the odoriferous oral cavity with the oral care composition to be tested.

The cleaning step again typically comprises brushing the teeth with the oral care composition, which is a toothpaste or dentifrice gel. Alternatively, the cleaning step may comprise rinsing the oral cavity with the oral care composition, which is a mouthwash or mouthrinse. The cleaning step preferably has a predetermined time period, and for example may take from 30 seconds to 2 minutes, typically about 1 minute. Typically, the cleaning is carried out within a period of from 0 to 5 minutes following the sampling of the second sample of exhaled breath from the oral malodor material-treated oral cavity using the fiber assembly 2.

Second Sampling of the Cleaned Oral Malodor Material-Containing Mouth Headspace

In a further testing step, a second sample of exhaled breath from the oral malodor material-treated and subsequently cleaned oral cavity is tested to provide a second test result representing a second amount of at least one oral malodor component detected in the exhaled breath. Optionally, the second sample is taken at a period from 30 to 60 minutes, topically 40 minutes, after the commencement of the initial cleaning step.

The testing was carried out as described above for the sampling of the cleaned mouth headspace. A further SPME fiber assembly 2 is used, and then the same gas chromatograph and mass spectrometry procedures are carried out as described above. This sampling provides a plurality of counts at a respective acquisition time for each component detected. Again, the method of the invention may be used to detect only a single component. However, in the preferred embodiments, plural components are detected, each having a respective acquisition time, and the counts at each acquisition time represents the amount of the respective component present. In some embodiments, the testing step adds together the counts representing the amounts of at least two or all of the detected oral malodor components in the respective sample of exhaled breath to provide a single quantified total count value for the sample of exhaled breath. The single quantified total count value represents oral malodor associated with the oral malodor material in the oral malodor material-containing and subsequently cleaned mouth headspace.

The second test result may be compared with the first test result to provide an indication of the ability of the oral care composition to refresh the oral cavity and reduce oral malodor resulting from exposure to the oral malodor material.

The testing protocols described above may be used to compare the performance of different oral care compositions in reducing oral malodor, in particular onion and/or garlic malodor. For example, a first oral care composition, formulated to provide oral malodor reduction, may be used as a test sample, and a second oral care composition may be used as a control sample.

The peaks in the chromatograms from the GC-MC readings can be converted into counts for the individual malodor component which can be identified by their individual acquisition times. The count data thus provides a numerical value for the detected amount of the respective malodor component.

The invention also provides for a composition for testing the efficacy of an oral care composition to reduce oral malodor comprising at least one compound selected from the group consisting of ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

In another embodiment of the invention, the composition for testing the efficacy of an oral care composition to reduce oral malodor comprising at least three compounds selected from the group consisting of ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

In another embodiment of the invention, the composition for testing the efficacy of an oral care composition to reduce oral malodor comprises ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

In another embodiment of the invention, a composition for testing the efficacy of an oral care composition to reduce oral malodor described above have no additional ingredients.

The invention also provides for an oral composition detected by any of the above described methods, wherein the oral care composition is a dentifrice, mouthwash, mouthrinse, toothpaste, gel, dental cream, chewing gum, or portable dosage article such as, without limitation, a lozenge, a mint, bead, wafer, lollipop, liquid formulated for oral application in a small portable nebulizer (spray bottle), liquid formulated for oral application in a small portable drop-generating bottle, or a soft pliable tablet which reduces oral malodor by at least one compound selected from the group consisting of ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid and comprises one or more of a carbonyl compound, a compound which encapsulate the furan or pyrrole compounds, tetrasodium pyrophospate, flavorants and combinations thereof.

In another embodiment of the detected oral care composition, the oral care composition reduces oral malodor at least three compounds selected from the group consisting of ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

In another embodiment of the detected oral care composition, the oral care composition reduces oral malodor from the combination of ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

The invention is illustrated in the following non-limiting examples.

EXAMPLES

Example 1

An in vitro test method according to the invention was used to study the performance of a toothpaste composition in reducing onion oral malodor.

A toothpaste was tested using an embodiment of the method of the invention to determine the ability (a) prophylactically to prevent onion malodor in the mouth headspace by brushing before applying the onion malodor material, hereinafter called the stimulus, and (b) to remove onion malodor in the mouth headspace by brushing after rinsing the oral cavity with the stimulus.

Step 1—First Cleaning of the Mouth Headspace

The volunteer subject brushed their teeth with the respective toothpaste for a period of 1 minute.

Step 2—Sampling of the Cleaned Mouth Headspace

The volunteer subject breathed through their mouth into a SPME (solid phase micro extraction) fiber assembly for a period of 1 minute so that a first sample of exhaled breath from the cleaned oral cavity was tested and the required oral malodor components were collected on the SPME fibers. The fiber assembly was prevented from direct contact with the mouth by a spacer tube of polymeric material. The fiber assembly comprised fused silica fibers having a 75 micron coating of Carboxen®/polydimethylsiloxane (CAR/PDMS) as the matrix active group, the fibre assembly having a black plain hub and being available from Supelco, of Bellefonte, Pa., USA. The volunteer human subject breathed in through the nose and out through the mouth into the tube and fiber assembly.

The oral malodor components collected in the fiber assembly were separated using gas phase chromatography. The gas phase chromatography employed a gas chromatograph (GC) sold under the trade name GC7890A by Agilent Technologies, Palo Alto, Calif., USA. In the gas chromatograph the oven temperature was held at 35° C. for 1 minute, and then the temperature was increased to 160° C. at a 15° C./min rate and held there for another 2.667 minutes. The total running time was 12 minutes. Helium was used as the carrier gas and the flow rate was 1 mL/min. The injector temperature was set up at 250° C. A SLBTM-5 ms GC column (30 m×0.25 mm×0.25 µm film thickness, available from Sigma-Aldrich, Bellefonte, Pa.) was used for the separation of the oral malodor components collected in the fiber assembly.

After the oral malodor components collected in the fiber assembly had been separated, an amount of the separated oral malodor components was determined using mass spectrometry to provide a quantification representing an amount of the oral malodor components in the sample of exhaled breath.

The mass spectrometer comprised a 7000MS Triple Quadrupole Mass Spectrometer available from Agilent Technologies, Palo Alto, Calif., USA. The non-ionization for solvent delay was from 0 to 0.5 minutes. The mass spectrometry detection was switched on at 0.5 minutes.

The mass spectrometer recorded a plurality of counts at a respective acquisition time for each component detected. Seven oral malodor components were detected, each having a respective acquisition time, and the counts at each acquisition time represented the amount of the respective component present.

In this Example, for detecting onion malodor, the oral malodor components detected were ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

When these particular oral malodor components were detected, the acquisition times were as follows using the 7000MS Triple Quadrupole Mass Spectrometer and the parameter settings as set out above.

From 0.5 to 3.0 minutes, ethanethiol was detected with a precursor ion at 57.8 and product ion at 31.3 and the collision energy was 20 eV. From 3.0 to 4.5 minutes, dimethyl sulfide was detected with a precursor ion at 93.7 m/z and product ion at 79.0 m/z and the collision energy was 20 eV. From 4.5 to 5 4 minutes, 3, 4-dimethylthiophene was detected with a precursor ion at 110.8 m/z and product ion at 77.1 m/z and the collision energy was 20 eV. From 5.4 to 5.8 minutes, methyl-1-propenyl disulfide was detected with a precursor ion at 119.7 m/z and product ion at 75.1 m/z and the collision energy was 10 eV. From 5.8 to 6.3 minutes, dimethyl trisulfide was detected with a precursor ion at 125.7 m/z and product ion at 79.0 m/z and the collision energy was 20 eV. From 6.3 to 7 7 minutes, dipropyl sulfide was detected with a precursor ion at 149.7 m/z and product ion at 43.2 m/z and the collision energy was 10 eV. From 7.7 to 8.5 minutes, 3-mercapto-2-mercapto methyl propanoic acid was detected with a precursor ion at 151.7 m/z and product ion at 88.0 m/z and the collision energy was 10 eV. The count total of each component was recorded to indicate the amount of that component which had been detected.

Step 3—Introducing Oral Malodor Material into the Mouth

Thereafter, the oral cavity of the volunteer subject was exposed to measured dose of onion malodor material. The exposure to oral malodor material was carried out about 15 to 20 minutes after the commencement of the initial cleaning of the oral cavity.

To prepare a measured dose of onion malodor material, approximately 0.5 gram of onion powder was suspended in 5 mL water, sonicated for 2 minutes, and filtered with a 0.45 µm PTFE filter. The onion odor was introduced into the oral cavity by rinsing the mouth with 3 mL of that onion malodor solution for 1 minute.

Step 4—First Sampling of the Malodorous Mouth Headspace

In a further testing step, a first sample of exhaled breath from the oral malodor material-treated oral cavity was tested to provide a first test result representing a first amount of at least one oral malodor component detected in the exhaled breath. The first sample was taken at a period of 20 minutes after the commencement of the initial cleaning step.

The testing was carried out as described above for the sampling of the cleaned mouth headspace. A further SPME fiber assembly 2 was used, and then the same gas chromatograph and mass spectrometry procedures were carried out as described above. This sampling provided a plurality of counts at a respective acquisition time for each component detected. Again, the method of the invention was used to detect the seven oral malodor components as in the previous sampling.

Step 5—Second Cleaning of the Mouth Headspace

Further testing was conducted to provide an indication of the ability of the oral care composition to refresh the oral cavity and reduce oral malodor resulting from previous exposure to the oral malodor material.

The oral care composition to be tested was used again to clean the oral cavity. The cleaning step again comprised brushing the teeth with the toothpaste for a time period of 1 minute. The cleaning was carried out within a period of from 0 to 5 minutes following the sampling of the first sample of exhaled breath from the oral malodor material-treated oral cavity.

Step 6—Second Sampling of the Malodorous then Cleaned Mouth Headspace

In a further testing step, similar to the first sampling tests, a second sample of exhaled breath from the oral malodor material-treated and subsequently cleaned oral cavity was tested to provide a second test result representing a second amount of the seven oral malodor components detected in the exhaled breath. The second sample was taken at a period of 40 minutes after the commencement of the initial cleaning step.

The testing was carried out as described above for the previous samplings. A further SPME fiber assembly was used, and then the same gas chromatograph and mass spectrometry procedures were carried out as described above. This sampling provided a plurality of counts at a respective acquisition time for each component detected. Again, the method of the invention was used to detect the seven oral malodor components as in the previous sampling.

Step 7—Comparison of Results of First and Second Samplings

The data from the chromatograms of the first and second samplings was analysed by comparing, for each of the seven detected oral malodor components, a quantification of the count values of the first and second samplings.

To determine the ability of the tested oral care composition prophylactically to prevent onion malodor in the mouth headspace, for each of the seven detected oral malodor components, the first and second count values are compared.

To determine the ability of the tested oral care composition to remove onion malodor already existing in the mouth headspace, for each of the seven detected oral malodor components, the first and second count values are compared.

By comparing the results for one oral care composition against another oral care composition, the efficacy of each oral care composition against oral malodor can be quantified using a robust and repeatable test. The efficacy for malodor removal can be expressed as a percentage reduction in the count value for a more effective composition as compared to a less effective composition.

Of course, other data analysis techniques may be employed to analyse the count data to provide an indication of the efficacy, absolute or comparative, of the tested oral care composition(s).

For each of the first and second samplings, the counts representing the amounts of all seven of the detected oral malodor components in the respective sample of exhaled breath were added together to provide a single quantified total count value for the sample of exhaled breath. The single quantified total count value represents oral malodor associated with the oral malodor material in the respective sampling.

Again, by comparing the single quantified total count values for one oral care composition against another oral care composition, the efficacy of each oral care composition against oral malodor can be quantified using a robust and repeatable test.

Example 2

An in vitro test method according to the invention was used to study the performance of different toothpaste compositions in reducing onion oral malodor.

A control toothpaste and a test toothpaste containing an onion malodor agent were measured on a volunteer using an embodiment of the method of the invention to determine their respective ability (a) prophylactically to prevent onion malodor in the mouth headspace by brushing before applying the stimulus, and (b) to remove onion malodor in the mouth headspace by brushing after rinsing the oral cavity with the stimulus. The same sequence of steps as described above for Example 1 was used. In each sequence, the control toothpaste and the test toothpaste were tested independently.

The same onion malodor material was used. All seven oral malodor components were determined in each of the three samplings. Compound 1 was ethanethiol, compound 2 was dimethyl sulfide, compound 3 was 3,4-dimethylthiophene, compound 4 was methyl-1-propenyl disulfide, compound 5 was dimethyl trisulfide, compound 6 was dipropyl sulfide and compound 7 was 3-mercapto-2-mercapto methyl propanoic acid.

The results for the malodor prophylactic test, analysing the count data from the first (after 20 minutes) and second (after 40 minutes) samplings, are shown for four different panelists are shown in Tables 2-5.

Key to Tables 2-5:
RT (retention time in minutes)
A (malodor compound number—(1) ethanethiol, (2) dimethyl sulfide, (3) 3,4-dimethylthoiphene, (4) methyl-1-propenyl disulfide, (5) trimethyl sulfide, (6) dipropyl sulfide and (7) 3-mercapto-2-mercaptomethyl propanoic acid.
First Sampling Data (Effectiveness of Toothpaste as Preventive Agent)
Control toothpaste—contains tetrasodium pyrophosphate (TSPP) and flavor
B (Control toothpaste—Malodor count from triple quad MS detector—exposure to onion solution 20 minutes after initial cleaning of the oral cavity)
C (Control toothpaste +1% composition containing carbonyl compounds—Malodor count from triple quad MS detector—exposure to onion solution 20 minutes after initial cleaning of the oral cavity)

D (% Malodor compound reduction—comparison of B vs. C)

Second Sampling Data (Effectiveness of Toothpaste in Refreshing and Removing Malodor)

Control toothpaste—contains tetrasodium pyrophosphate (TSPP) and flavor

E (Control toothpaste—Malodor count from triple quad MS detector—exposure to onion solution 20 minutes after second cleaning of the oral cavity; 40 minutes after initial cleaning)

F (Control toothpaste +1% composition containing carbonyl compounds—Malodor count from triple quad MS detector—exposure to onion solution 20 minutes after second cleaning of the oral cavity; 40 minutes after initial cleaning).

G (% Malodor compound reduction—comparison of E vs. F)

TABLE 2

| RT | A | B | C | D | E | F | G |
|---|---|---|---|---|---|---|---|
| 1.7 | (1) | 25706 | 4631 | 82.0% | 5886 | 1532 | 74.0% |
| 3.3 | (2) | 177750 | 40019 | 77.5% | 2924 | 1400 | 52.1% |
| 5.2 | (3) | 59800 | 15745 | 73.7% | 4416 | 1279 | 71.0% |
| 5.6 | (4) | 58797 | 13376 | 77.3% | 2604 | 646 | 75.2% |
| 6 | (5) | 9277 | 2653 | 71.4% | 354 | 113 | 68.1% |
| 7.5 | (6) | 31104 | 1221 | 96.1% | 5340 | 94 | 98.2% |
| 8.1 | (7) | 525 | 114 | 78.3% | 35 | 3 | 91.4% |
| Total | | 362959 | 77759 | 78.6% (avg.) | 21559 | 5067 | 76.5% (avg.) |

TABLE 3

| RT | A | B | C | D | E | F | G |
|---|---|---|---|---|---|---|---|
| 1.7 | (1) | 10536 | 3526 | 66.5% | 2071 | 1127 | 45.6% |
| 3.3 | (2) | 53569 | 17602 | 67.1% | 1302 | 224 | 82.8% |
| 5.2 | (3) | 36140 | 13762 | 61.9% | 1117 | 367 | 67.1% |
| 5.6 | (4) | 26305 | 9659 | 63.3% | 775 | 730 | 5.8% |
| 6 | (5) | 6339 | 2734 | 56.9% | 73 | 56 | 23.3% |
| 7.5 | (6) | 6634 | 1696 | 74.4% | 506 | 58 | 88.5% |
| 8.1 | (7) | 438 | 238 | 45.7% | 1 | 0 | 100.0% |
| Total | | 139961 | 49217 | 64.8% (avg.) | 5845 | 2562 | 56.2% (avg.) |

TABLE 4

| RT | A | B | C | D | E | F | G |
|---|---|---|---|---|---|---|---|
| 1.7 | (1) | 10523 | 5591 | 46.9% | 1986 | 1186 | 40.3% |
| 3.3 | (2) | 83807 | 46545 | 44.5% | 1738 | 242 | 86.1% |
| 5.2 | (3) | 45087 | 26828 | 40.5% | 1457 | 722 | 50.5% |
| 5.6 | (4) | 38305 | 20633 | 46.1% | 1513 | 184 | 87.8% |
| 6 | (5) | 14653 | 8056 | 45.0% | 127 | 20 | 84.3% |
| 7.5 | (6) | 9378 | 2747 | 70.7% | 298 | 110 | 63.1% |
| 8.1 | (7) | 915 | 297 | 67.5% | 1 | 1 | 0.00% |
| Total | | 202668 | 110697 | 45.4% (avg.) | 7120 | 2465 | 65.4% (avg.) |

TABLE 5

| RT | A | B | C | D | E | F | G |
|---|---|---|---|---|---|---|---|
| 1.7 | (1) | 22289 | 7351 | 67.0% | 5014 | 3145 | 37.3% |
| 3.3 | (2) | 196202 | 75766 | 61.4% | 5107 | 1193 | 76.6% |
| 5.2 | (3) | 91346 | 59491 | 34.9% | 3707 | 2244 | 39.5% |
| 5.6 | (4) | 85212 | 36360 | 57.3% | 1156 | 376 | 67.5% |

TABLE 5-continued

| RT | A | B | C | D | E | F | G |
|---|---|---|---|---|---|---|---|
| 6 | (5) | 33025 | 7744 | 76.6% | 321 | 78 | 75.7% |
| 7.5 | (6) | 14416 | 5154 | 64.3% | 2358 | 397 | 83.2% |
| 8.1 | (7) | 2676 | 772 | 71.2% | 19 | 4 | 79.0% |
| Total | | 445166 | 192638 | 56.7% (avg.) | 17682 | 7437 | 57.9% (avg.) |

The above data shows that the SPME—GC/MS method of the invention allows for rapid determination that the toothpaste with a carbonyl compound provided lower counts overall for the individual malodor compounds and compared with the same toothpaste without a carbonyl compound and was able to provide this data for the seven malodor compounds with only one test sample. This provided a quantified indication of the prophylactic efficacy and ability to reduce malodor components by the test toothpaste against oral malodor.

By detecting the all of the major components of malodor by the SPME—GC/MS method of the invention, it was confirmed that the reduction in malodor came from an actual decrease in the amount of malodor compounds and was not the result of masking, i.e. the present of a carbonyl compound improved malodor removal better than a comparable toothpaste with TSPP and flavor.

Moreover, it could also be seen that while there was a generalized reduction in malodor compounds, there were differences in effectiveness between panelists. For example, the panelist in Table 3 could maintain using the 1% composition containing a carbonyl compound after the initial malodor challenge (64.8% reduction relative to control), but switch compositions after the second malodor challenge (56.2% reduction relative to control) to a more effective formulation. In contrast, the panelist in Table 4 may desire to switch from 1% composition containing a carbonyl compound after the initial malodor challenge (45.4% % reduction relative to control), but use this composition after the second malodor challenge (65.4% reduction relative to control).

By having this rapid access to data related to malodor treatment, not only can improved malodor compositions be developed, but such compositions can either be selected over other less effective compositions and facilitate the tailoring of compositions to an individual's needs by incorporating different or additional agents to reduce malodor compounds (e.g. compound (3) was reduced in all four panelists, but within a range of 34.9% to 73.7%).

The presently claimed method provides a means for selecting the proper dentifrice for providing a prophylactic effect for treating malodor and also for selecting the proper dentifrice for providing a reduction in malodor components.

While particular embodiments of the invention have been illustrated and described, it will be obvious to those skilled in the art that various changes and modifications may be made without departing from the scope of the invention as defined in the appended claims.

The invention claimed is:

1. A method for testing the efficacy of and selecting an oral care composition to reduce oral malodor, wherein the method comprises the steps of:
   a1. cleaning at least a part of the oral cavity with an oral care composition and testing the cleaned oral cavity to provide a baseline amount of at least one oral malodor component detected in the exhaled breath;

b1. exposing the oral cavity to an oral malodor material containing the at least one oral malodor component;

c1. a first sample of exhaled breath from the oral cavity to detect a first amount of the at least one oral malodor component in the exhaled breath which is a representation of the prophylactic effect of the oral care composition; and d1. comparing the first amount of the at least one oral malodor component detected in the exhaled breath after cleansing with an oral care composition with a first amount from cleansing with a different oral care composition and selecting the oral care composition with the lower first amount for a method of providing prophylactic effect against at least one malodor component in the oral cavity;

wherein the oral malodor material is selected from at least one of onion and garlic;

wherein the cleaning step comprises: (i) brushing the teeth with the oral care composition which is a toothpaste or dentifrice gel and/or (ii) rinsing the oral cavity with the oral care composition which is a mouthwash or mouthrinse; and wherein the oral malodor component is the combination of ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

2. The method of claim 1, wherein each obtaining step includes the sub-steps of:

i. collecting the at least one oral malodor component on solid phase micro extraction (SPME) fibers;

ii. separating the collected at least one oral malodor component using chromatography; and iii. determining an amount of the separated at least one oral malodor component using mass spectrometry to provide a quantification representing an amount of the at least one oral malodor component in the respective sample of exhaled breath.

3. The method of claim 2, wherein the chromatography is gas phase chromatography (GC) and/or the mass spectrometry (MS) is triple quadrupole mass spectrometry.

4. The method of claim 3, wherein step b1 or b2 is carried out from 10 to 30 minutes after step a1 or a2, respectively, step c1 or c2 is carried out from 15 to 45 minutes after step a1 or a2, respectively, and step e1 or e2 is carried out from 30 to 60 minutes after step a1 or a2, respectively.

5. The composition for testing the efficacy of an oral care composition to reduce oral malodor using the method of claim 1, which comprises the combination of ethanethiol, dimethyl sulfide, 3,4-dimethylthoiphene, methyl-1-propenyl disulfide, trimethyl sulfide, dipropyl sulfide and 3-mercapto-2-mercaptomethyl propanoic acid.

6. The composition of claim 5, wherein there are no additional ingredients.

* * * * *